(12) United States Patent
Budroni et al.

(10) Patent No.: US 10,144,697 B2
(45) Date of Patent: Dec. 4, 2018

(54) GAS PHASE PRODUCTION OF ALKYL ALKANOATES

(71) Applicant: Dow Global Technologies LLC, Midland, MI (US)

(72) Inventors: Gerolamo Budroni, Terneuzen (NL); Steven L. F. Corthals, Wachtebeke (BE)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 15/558,287

(22) PCT Filed: Mar. 22, 2016

(86) PCT No.: PCT/US2016/023571
§ 371 (c)(1),
(2) Date: Sep. 14, 2017

(87) PCT Pub. No.: WO2016/154196
PCT Pub. Date: Sep. 29, 2016

(65) Prior Publication Data
US 2018/0057441 A1    Mar. 1, 2018

Related U.S. Application Data

(60) Provisional application No. 62/138,754, filed on Mar. 26, 2015.

(51) Int. Cl.
| | | |
|---|---|---|
| C07C 2/82 | (2006.01) | |
| C07C 2/84 | (2006.01) | |
| C07C 11/04 | (2006.01) | |
| C07C 67/38 | (2006.01) | |
| C07C 69/24 | (2006.01) | |
| C07C 67/343 | (2006.01) | |

(52) U.S. Cl.
CPC ............ C07C 67/38 (2013.01); C07C 2/82 (2013.01); C07C 2/84 (2013.01); C07C 67/343 (2013.01); Y02P 20/52 (2015.11)

(58) Field of Classification Search
CPC .. C07C 2/84; C07C 67/38; C07C 2/82; C07C 67/343
See application file for complete search history.

(56) References Cited

U.S. PATENT DOCUMENTS

| | | | | |
|---|---|---|---|---|
| 3,501,518 A | * | 3/1970 | Bittler | ............... C07C 51/14 554/129 |
| 5,015,799 A | * | 5/1991 | Walker | ............... C07C 2/82 585/415 |
| 7,906,699 B2 | * | 3/2011 | Benderly | ............. C07C 5/42 585/654 |

FOREIGN PATENT DOCUMENTS

| | | | |
|---|---|---|---|
| CN | 102093157 | * | 6/2011 |
| WO | 199622265 A1 | | 7/1996 |
| WO | 2011059855 A1 | | 5/2011 |
| WO | 2014209170 A1 | | 12/2014 |

OTHER PUBLICATIONS

English translation of CN102093157, Jun. 15, 2011, pp. 1-6 (Year: 2011).*
Vit, Z., et al; Hydroformylation of Ethylene Over Cobalt, Nickel, Molybdenum, CoMo and NiMo Alumina Supported Sulfide Catalysts; Applied Catalysts A: General, vol. 116, pp. 259-268, 1994.

* cited by examiner

*Primary Examiner* — Pancham Bakshi
*Assistant Examiner* — Mark R Luderer
(74) *Attorney, Agent, or Firm* — Edward L. Brant

(57) ABSTRACT

An alkane-containing stream is reacted to produce an alkene, which is carbonylated to produce an alkyl alkanoate, e.g., methyl propanoate, by a gas phase process comprising the step of contacting under carbonylation conditions the alkene, e.g., ethylene, carbon monoxide, an alkanol, e.g., methanol, and a solid sulfide-based metal catalyst.

14 Claims, No Drawings

GAS PHASE PRODUCTION OF ALKYL ALKANOATES

FIELD OF THE INVENTION

This invention relates to the gas phase production of alkyl alkanoates. In one aspect, the invention is the gas-phase production of alkyl propanoates by the carbonylation of ethylene with an alkanol using a heterogeneous sulfide-based metal catalyst, wherein the ethylene is produced from a methane-rich gas, such as shale gas.

BACKGROUND OF THE INVENTION

The development of improved extraction methods for shale gas and natural gas are providing an abundant source of hydrocarbon feedstocks. These feedstocks are gas mixtures that typically contain 80-99% methane, 1-20% ethane, 1-5% higher hydrocarbons and other non-hydrocarbon constituents, such as $CO_2$ and nitrogen. While the exploitation of wet shale gas is ramping up and new ethane crackers are being built, the large fraction of methane from shale gas today is mainly used as fuel or as a feedstock for syngas production.

Converting the methane directly into chemical products presents a technical challenge. The oxidative coupling of methane (OCM) is one of the most explored routes for the direct conversion of methane into products. The OCM reaction to ethylene is: $2\ CH_4 + O_2 \rightarrow C_2H_4 + 2H_2O$. Despite the fact that intense research was dedicated to OCM catalyst development, the yields of ethylene and other desired C2+ hydrocarbon molecules appear to have reached a maximum of about 20-30%, suggesting a limit. The main issue with the OCM process is that oxygen is more reactive with the products than with methane. As the concentration of products increases, so does the rate of side reactions. Since the OCM reaction occurs at high temperatures, e.g., 400-1000° C., the choice of the catalyst has little effect on the speed of the side reaction, and the majority of methane is non-selectively oxidized to carbon dioxide. The second main issue with OCM is the costly separation of the ethylene out of the OCM product stream, which contains unreacted methane, $H_2$, CO, $H_2O$, $CO_2$ and $C_{2+}$ hydrocarbons such as, but not limited to, ethylene and ethane. The composition of the product of an OCM process not only depends on the catalyst type, but also on the type of oxygen source, such as air or pure oxygen, and operating conditions ($CH_4/O_2$ ratio, P, T, contact time, and reactor type). The influence of catalyst type, operating conditions and cofeed options on the product composition of the OCM process is known to those skilled in the art.

It would be desirable to have a process that could take advantage of the increased supply of shale gas to convert it into useful chemical products while avoiding the costly separation of ethylene from the product stream.

SUMMARY OF THE INVENTION

In one embodiment the invention is a process comprising: (a) providing a gas feed stream comprising >1 mol % of an alkane; (b) at least partially converting the alkane to produce a gaseous first intermediate stream comprising water, unreacted alkane, and >1 mol % of an alkene; (c) removing the majority of the water from the gaseous first intermediate stream to produce a gaseous second intermediate stream comprising at least one alkene; and (d) contacting under gas phase carbonylation conditions the gaseous second intermediate stream, carbon monoxide gas, an alkanol gas and a solid sulfide-based metal catalyst to produce an alkyl alkanoate.

In one embodiment, the invention is a process comprising: (a) providing a gas feed stream comprising >1 mol % of an alkane; (b) at least partially converting the alkane to produce a gaseous first intermediate stream comprising water, other hydrocarbons, $H_2$, CO, $CO_2$, unreacted alkane, and >1 mol % of an alkene; (c) removing the majority of the water from the gaseous first intermediate stream to produce a gaseous second intermediate stream comprising at least one alkene, other hydrocarbons, $H_2$, CO, $CO_2$ and unreacted alkane; and (d) contacting under gas phase carbonylation conditions the gaseous second intermediate stream, carbon monoxide gas, an alkanol gas and a solid sulfide-based metal catalyst to produce an alkyl alkanoate.

In another embodiment, the invention is a process comprising: (a) providing a gas feed stream comprising >1% of methane; (b) at least partially converting the methane via an OCM process to produce a gaseous first intermediate stream comprising water, other hydrocarbons, $H_2$, CO, $CO_2$, unreacted methane, and >1% of ethylene; (c) removing the majority of the water from the gaseous first intermediate stream to produce a gaseous second intermediate stream comprising ethylene, other hydrocarbons, $H_2$, CO, $CO_2$ and unreacted methane; and (d) contacting under carbonylation conditions the gaseous second intermediate stream, carbon monoxide gas, gaseous methanol and a solid sulfide-based metal catalyst to produce methyl propanoate.

Surprisingly high selectivity to the alkyl alkanoate is obtained by this gas phase process, while advantageously not requiring a costly alkene/alkane separation prior to the carbonylation reaction.

DETAILED DESCRIPTION OF THE PREFERRED EMBODIMENT

Definitions

All references to the Periodic Table of the Elements refer to the Periodic Table of the Elements published at page 1-10 of the CRC Handbook of Chemistry and Physics, 71$^{st}$ Ed. (1990-1991). Also, any references to a Group or Groups shall be to the Group or Groups reflected in this Periodic Table of the Elements using the IUPAC system for numbering groups. Unless stated to the contrary, implicit from the context, or customary in the art, all parts and percentages are based on weight and all test methods are current as of the filing date of this disclosure. Percentages given in connection with a gas stream are given in mole percent based on the total moles present in the stream. For purposes of United States patent practice, the contents of any referenced patent, patent application or publication are incorporated by reference in their entirety (or its equivalent US version is so incorporated by reference) especially with respect to the disclosure of synthetic techniques, product and processing designs, polymers, catalysts, definitions (to the extent not inconsistent with any definitions specifically provided in this disclosure), and general knowledge in the art.

The numerical ranges in this disclosure are approximate, and thus may include values outside of the range unless otherwise indicated. Numerical ranges include all values from and including the lower and the upper values, in increments of one unit, provided that there is a separation of at least two units between any lower value and any higher value. As an example, if a compositional, physical or other property, such as, for example, molecular weight, weight percentages, etc., is from 100 to 1,000, then the intent is that all individual values, such as 100, 101, 102, etc., and sub ranges, such as 100 to 144, 155 to 170, 197 to 200, etc., are expressly enumerated. For ranges containing values which are less than one or containing fractional numbers greater than one (e.g., 1.1, 1.5, etc.), one unit is considered to be 0.0001, 0.001, 0.01 or 0.1, as appropriate. For ranges containing single digit numbers less than ten (e.g., 1 to 5), one unit is typically considered to be 0.1. These are only examples of what is specifically intended, and all possible combinations of numerical values between the lowest value and the highest value enumerated, are to be considered to be expressly stated in this disclosure. Numerical ranges are provided within this disclosure for, among other things, the amounts of the various reactants in and the operating conditions of the inventive process.

"Composition" and like terms mean a mixture or blend of two or more components.

"Carbonylation conditions" and like terms mean the temperature, pressure and other conditions necessary for an alkene, carbon monoxide and an alkanol, one or more of which is at least partially in the form of a gas, to react with one another over and in contact with a solid sulfide-based catalyst to form an alkyl alkanoate. In one embodiment each of the alkene, CO and alkanol are at least partially in the form of a gas. In one embodiment each of the alkene, CO and alkanol are completely or nearly completely in the form of a gas.

"Condensation conditions" and like terms mean the temperature, pressure and other conditions necessary for an alkyl alkanoate and an aldehyde, each in the form of a gas, to react with one another over and in contact with a solid condensation catalyst to form an alkyl ester of an aliphatic carboxylic acid.

"Halogen-free carbonylation conditions" and like terms mean carbonylation conditions in which halogen in any form is absent or essentially absent from the space in which the alkene, CO and alkanol are contacted over a sulfide-based metal catalyst to form an alkyl alkanoate. "Essentially absent" means that any halogen present in the reaction space is present in an amount that does not materially affect the conversion or selectivity of the reactants to the desired alkyl alkanoate. The source of such halogen can be, for example, from one or more of the feeds to the reaction or the catalyst (as, for example, a contaminant), or from the surface of a piece of equipment, etc. In one embodiment "halogen-free" means less than (<)1000 parts per million (ppm), preferably <10 ppm and more preferably <1, ppm based on the combined weight of the reactants.

For the purposes of this disclosure, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic, saturated and unsaturated, organic compounds that can be substituted or unsubstituted.

For the purposes of this disclosure, the term "alkane" refers to an aliphatic hydrocarbon characterized by a straight or branched carbon chain having the formula $C_nH_{2n+2}$. Examples of alkanes include methane, ethane, propane, butane, and the like.

For the purposes of this disclosure, the term "alkene" refers to a class of hydrocarbons characterized by a straight or branched carbon chain having the formula $C_nH_{2n}$. Examples of alkenes include ethene, propene, butenes, pentenes and the like.

The process of the invention employs: in step (b) a gas feed stream comprising an alkane; and in step (d) an alkene, carbon monoxide gas, an alkanol gas and a solid sulfide-based metal catalyst.

The gas feed stream of step (a) comprises at least 1 mole % of an alkane, and preferably comprises at least 20 mole % of an alkane. Advantageously, the alkane comprises from 1 to 20 carbon atoms, preferably from 1 to 8 carbon atoms, and more preferably from 1 to 5 carbon atoms. Examples of alkanes are given hereinabove. Methane is the preferred alkane. The gas feed stream may comprise mixtures of alkanes. In one embodiment of the invention, the gas feed stream can be a gas stream from shale gas or natural case production, either with or without treatment to remove various components. Treatment methods are well known to those skilled in the art. In various embodiments of the invention, the alkane-containing gas comprises at least 20 mole percent alkane, at least 50 mole percent alkane, or at least 80 mole percent alkane. In one embodiment of the invention, the gas feed stream is a methane-containing gas mixture that contains from 80-99% methane, from 1-20% ethane, and from 1-5% other hydrocarbons and other non-hydrocarbon constituents, such as $CO_2$ and nitrogen, the percentage of components totaling 100% on a molar basis.

Step (b)

The process of the invention includes a step in which an alkane is at least partially converted to an alkene from a gas mixture comprising an alkane and other components. For the production of the alkene from the alkane, a number of processes known to those skilled in the art can be envisioned such as, for example, OCM, conversion of methane into syngas and subsequent Fischer-Tropsch reactions, methane pyrolysis, ethane cracking etc. OCM is preferred when the alkane is methane. The alkane-containing gas feed stream is treated in step (b) to at least partially convert the alkane into at least one alkene. The product of step (b), or the gaseous first intermediate stream, is a gas stream that comprises the alkene, unreacted alkane, $H_2$, CO, $CO_2$ and other hydrocarbons. In one embodiment of the invention, the gaseous first intermediate stream comprises from 1-25% alkene and from 1 to 66% alkane, with the remainder being water, $H_2$, CO, $CO_2$, and optionally other hydrocarbons. In one embodiment of the invention, in which OCM is employed, the gaseous first intermediate stream comprises from 1 to 30% ethylene, from 1 to 60% methane, with the remainder being water, $H_2$, CO, $CO_2$, and optionally other hydrocarbons. In one embodiment of the invention, the conversion process of step (b) comprises OCM. The feed to the OCM reactor comprises methane and oxygen. The oxygen may be supplied as an oxygen-containing gas, such as air or industrially pure oxygen. The molar ratio of methane to oxygen is from 0.1:1 to 25:1, or preferably from 2:1 to 5:1.

The OCM reaction is well known to those skilled in the art. Suitable reaction conditions and process configurations can be selected to obtain the desired product. The temperature and pressure of the OCM reaction are not particularly critical. For example, the temperature of the reaction can be from 400° C. to 1000° C., or from 700° C. to 900° C. The pressure can be from 0.08 to 2 MPa, or from 0.1 to 1 MPa. Suitable catalysts for the OCM reaction are well known to those skilled in the art, and examples of such include mixed oxide catalysts such as, for example, Li—MgO and Mn—$Na_2WO_4$/$SiO_2$. The OCM reaction can be conducted in any suitable equipment. Those skilled in the art are readily able to determine the specifications for suitable equipment and develop suitable equipment designs.

The OCM process can optionally involve cofeeding to the front or back end of the OCM reactor. This will influence the composition of the product of the OCM process. For example, cofeeding water in front of the OCM reactor has an influence on the $CO_2$ content of the OCM product stream. Similarly, ethane can be cofed towards the outlet of the OCM reactor, and this leads to an increased ethylene yield.
Step (c)

Step (c) of the process comprises removing the majority of the water from the gaseous first intermediate stream to produce a gaseous second intermediate stream comprising unreacted alkane, at least one alkene, optionally other hydrocarbons, $H_2$, CO, and $CO_2$. Techniques for removing water from a gaseous stream are well known to those skilled in the art. Thus, this removal may be accomplished by any suitable means including, e.g., condensation, including condensation due to compression. In one embodiment of the invention, in order to prevent side reactions of the desired alkene, the gaseous first intermediate stream can be quenched after the reaction of step (b), e.g., in a quench tower. The conditions for the water removal step are not particularly critical.
Production of the Alkyl Alkanoate—Step (d)

The carbonylation step (d), converts the alkene in the gaseous second intermediate stream to the desired alkanoate product. Any alkane passing through the carbonylation reactor can be recycled to step (b). Accordingly, the process can be used with OCM, and related, processes without the need to perform on the OCM product stream a costly and difficult separation of alkenes from alkanes. In one embodiment, the invention is a process for the production of an alkyl propanoate from ethylene, carbon monoxide and the alkanol. The ethylene is provided, at least in part or entirely, by the gaseous intermediate feed stream.
Carbonylation Reactants The alkanol, i.e., alcohol, is typically a $C_{1-30}$ alkanol which may contain one or more substituents such as a cyano, carbonyl, alkoxy or aryl group. Illustrative alkanols include, but are not limited to, methanol, ethanol, propanol, 2-propanol, 2-butanol, t-butyl alcohol and capryl alcohol. For purposes of this invention, polyhydroxyl compounds such as diols and sugars, are considered alkanols that can be used in the practice of this invention. Methanol is the preferred alkanol. Mixtures of alkanols may be employed.

The carbon monoxide can be used neat or in combination with one or more other gases. In one embodiment of the invention, these other gases are inert with respect to the reaction reagents, products and by-products of the carbonylation reaction under reaction conditions. Examples of these other gases include, but are not limited to, nitrogen, carbon dioxide and the noble gases. In one embodiment of the invention, the carbon monoxide may be provided, at least in part or entirely, by the gaseous second intermediate stream.
Carbonylation Catalyst The carbonylation catalyst is a sulfide-based catalyst, particularly a metal sulfide catalyst, more particularly a solid, sulfide-based metal catalyst. The catalyst can comprise one or more metals. Typically the catalyst comprises at least one Group VIII metal, e.g., iron, cobalt, nickel, rhodium, etc., and it can contain one or more other metals as well, e.g., a Group IA metal such as potassium or another transition metal such as titanium, vanadium, chromium, manganese, copper, zinc, tungsten and the like. The catalyst is a sulfide, which means that at least one metal of the catalyst is bonded covalently or ionicly to at least one sulfur atom. Suitable catalysts for use in the carbonylation step include, but are not limited to, iron sulfide, cobalt sulfide, rhodium sulfide with potassium promoter, and nickel sulfide, with cobalt sulfide being preferred.

Metal sulfides are well known in the art, and they can be prepared by various processes, e.g., precipitation/coprecipitation. For example, cobalt sulfide can be prepared by precipitation of an aqueous solution of $(NH_4)_2S$ and an aqueous cobalt salt solution, such as a cobalt nitrate solution. The precipitate is filtered, dried and treated in a furnace at, for example 500° C., under a nitrogen gas blanket. Purchased cobalt sulfides are also effective catalysts such as, for example CAS 1317-42-6 available from such suppliers as Sigma Aldrich and Materion.

The carbonylation catalyst can be supported. Examples of suitable supports include alumina, alpha alumina, gamma alumina, silica, silica-alumina, zeolite, magnesia, magnesium hydroxide, titania, calcium carbonate, activated carbon, and the like. The preparation of supported catalysts is well known in the art.
Carbonylation Process Conditions and Equipment The carbonylation reaction is conducted in the gas phase over a solid catalyst. As such, the alkene, CO and alkanol are introduced as gases and contacted with one another over and in contact with a solid catalyst bed. The reactants can be introduced in a single or multiple feed streams. In various embodiments of the invention, the molar ratio of CO to alkene is at least 1:1, at least 2:1, from 2:1 to 50:1 or from 4:1 to 15:1. In various embodiments of the invention, the molar ratio of alkene to alkanol is at least 0.1:1, at least 0.5:1, from 0.1:1 to 10:1 or from 0.2:1 to 2:1.

Although the carbonylation process can be operated in either a continuous or batch mode, the process is typically and preferably operated in a continuous mode.

The carbonylation temperature is advantageously from 120° C. to 450° C., preferably from 250° C. to 380° C. and more preferably from 280° C. to 340° C. The total pressure of the process is advantageously is from 0.1 to 20 MPa, and preferably is from 1.5 to 6 MPa. The space velocity of the process is advantageously from 100 to 1,000,000 liters of gas feed per liter of catalyst per hour (L/L*h), and preferably is from 500 to 5,000 L/L*hr.

In one embodiment, the carbonylation reaction is conducted in a high-pressure, fixed-bed reactor. In one embodiment, the reactor is a tube reactor. In a typical protocol the temperature and pressure are slowly increased to the reaction conditions. The catalyst can be exposed to a feed consisting of an inert gas (such as nitrogen or helium), hydrogen, small amounts of $H_2S$, carbon monoxide, olefins, alkanols and any combination of the above. In one embodiment of the invention, at least part of the feed to the carbonylation reactor comprises the gaseous intermediate feed stream. The effluent gas from the carbonylation reactor can be analyzed via suitable analytical techniques such as, for example, gas chromatography to determine the product composition and the amount of CO converted.

In one embodiment, the reactor is a trickle bed reactor in which the carbonylation catalyst is a solid and at least one of the reactants is at least partially in the gas phase. Typically, the ethylene and carbon monoxide are completely gaseous but the alkanol, depending upon its boiling point and the carbonylation conditions, may be partially or totally liquid. For purposes of this invention, a process, such as that conducted in a trickle-bed reactor, is considered a gas phase process as long as at least one of the alkene, CO and alkanol is at least partially, preferably mostly and more preferably completely or nearly completely, in the gas phase. In such a process, the alkene and CO advantageously are completely or nearly completely in the gas phase under carbonylation conditions.

The product of step (d) is an alkyl alkanoate. In one embodiment of the invention, ethylene, CO, methanol and a solid sulfide-based metal catalyst are contacted under carbonylation conditions sufficient to form methyl propionate, which is also called methyl propanoate.

Production of Alkyl Esters of Propionic Acids

In one embodiment of the invention, the alkyl alkanoate made in the process described above is condensed with an aldehyde to form an alkyl ester of an aliphatic carboxylic acid. When the alkyl alkanoate is methyl propanoate and the aldehyde is formaldehyde, the product is methyl methacrylate (MMA). The equipment, conditions and protocol of this condensation reaction are well known to those of skill in the art.

A preferred embodiment of the invention comprises: (a) providing a gas feed stream comprising >1 mol % of methane; (b) at least partially converting the methane via an OCM process to produce a gaseous first intermediate stream comprising water, $H_2$, CO, $CO_2$, unreacted methane, other hydrocarbons, and >1 mol % of ethylene; (c) removing the majority of the water from the gaseous first intermediate stream to produce a gaseous second intermediate stream comprising ethylene, other hydrocarbons, $H_2$, CO, $CO_2$ and unreacted methane; and (d) contacting under carbonylation conditions the gaseous second intermediate stream, carbon monoxide gas, gaseous methanol and a solid sulfide-based metal catalyst to produce methyl propanoate.

SPECIFIC EMBODIMENTS OF THE INVENTION

Example 1

A cobalt sulfide catalyst is prepared by precipitation of an aqueous solution of $(NH_4)_2S$ (20%) and a 1.2 molar aqueous cobalt nitrate solution. The precipitate is filtered, dried at 50° C. for 4 hours and treated in a furnace at 500° C. under a nitrogen gas atmosphere.

In a fixed-bed, high pressure microreactor, the cobalt sulfide catalyst is employed at 5 MPa using the feed composition shown in Table 1 in a temperature and space velocity range of 280-290° C. and 1700-4000 L/L*h as described below for 3 days. The feed is typical of a dried outlet stream of an OCM process, and is shown in Table 1. The results are shown in Table 2. Selectivities are mole % C product based.

TABLE 1

| Feed composition | | | | | | | |
|---|---|---|---|---|---|---|---|
| CO (vol %) | $H_2$ (vol %) | MeOH (vol %) | $C_2H_4^*$ (vol %) | $N_2$ (vol %) | $CO_2$ (vol %) | $CH_4$ (vol %) | $C_2H_6$ (vol %) |
| 30 | 5 | 2 | 4 | 10 | 7 | 40 | 2 |

TABLE 2

| Catalyst performance for cobalt sulfide at 5 MPa. | | | | | | | |
|---|---|---|---|---|---|---|---|
| SV, L/L*h | Temp, ° C. | Conv_ C2H4(%) | Sel %_ MP | Sel %_ MA | Sel %_ HC | Sel %_ CO2 | Sel %_ propanol/al |
| 4000 | 280 | 46 | 83 | <1 | 14 | <1 | 2 |
| 4000 | 290 | 53 | 83 | <1 | 14 | <1 | 2 |

TABLE 2-continued

| Catalyst performance for cobalt sulfide at 5 MPa. | | | | | | | |
|---|---|---|---|---|---|---|---|
| SV, L/L*h | Temp, ° C. | Conv_ C2H4(%) | Sel %_ MP | Sel %_ MA | Sel %_ HC | Sel %_ CO2 | Sel %_ propanol/al |
| 2000 | 280 | 64 | 77 | <1 | 20 | <1 | 2 |
| 2000 | 290 | 69 | 74 | <1 | 23 | <1 | 2 |

Sel %_MP: selectivity to methyl propanoate,
Sel %_MA: selectivity to methyl acetate,
Sel %_HC = sum selectivities of $C_2$ to $C_6$ alkanes and $C_3$ to $C_6$ alkenes.

Despite the presence of $CO_2$, $H_2$, $CH_4$ and $C_2H_6$ in the feed stream, selectivities to methyl propanoate are surprisingly good at up to 83%.

What is claimed is:

1. A process comprising: (a) providing a gas feed stream comprising >1 mol % of an alkane; (b) at least partially converting the alkane to produce a gaseous first intermediate stream comprising water, unreacted alkane, and >1 mol % of an alkene; (c) removing the majority of the water from the gaseous first intermediate stream to produce a gaseous second intermediate stream comprising at least one alkene; and (d) contacting under gas phase carbonylation conditions the gaseous second intermediate stream, carbon monoxide gas, an alkanol gas and a solid sulfide-based metal catalyst to produce an alkyl alkanoate, wherein the carbonylation conditions include a temperature from 200° C. to 400° C. and a pressure from 0.1 MPa to 10 MPa.

2. The process of claim 1 comprising: (a) providing a gas feed stream comprising >1 mol % of an alkane; (b) at least partially converting the alkane to produce a gaseous first intermediate stream comprising water, other hydrocarbons, $H_2$, CO, $CO_2$, unreacted alkane, and >1 mol % of an alkene; (c) removing the majority of the water from the gaseous first intermediate stream to produce a gaseous second intermediate stream comprising at least one alkene, other hydrocarbons, $H_2$, CO, $CO_2$ and unreacted alkane; and (d) contacting under gas phase carbonylation conditions the gaseous second intermediate stream, carbon monoxide gas, an alkanol gas and a solid sulfide-based metal catalyst to produce an alkyl alkanoate.

3. The process of claim 1 wherein the alkene is of the formula $C_nH_{2n}$, in which n is from 2 to 12, and the alkanol comprises from 1 to 30 carbon atoms.

4. The process of claim 1 wherein the alkane is methane and the alkene is ethylene.

5. The process of claim 1 wherein the solid, sulfide-based metal catalyst comprises one or more of iron, cobalt, rhodium, and nickel.

6. The process of claim 1 wherein the catalyst is supported.

7. The process of claim 1 wherein the carbonylation conditions are halogen-free.

8. The process of claim 1 in which the alkanol comprises 1-30 carbon atoms.

9. The process of claim 1 in which the alkanol is methanol.

10. The process of claim 1 wherein the alkane is methane, and step (b) comprises OCM.

11. The process of claim 1 wherein the alkyl alkanoate is methyl propanoate.

12. The process of claim 1 further comprising: (e) contacting under condensation conditions the alkyl alkanoate with an aldehyde to produce an alkyl ester of an aliphatic carboxylic acid, and wherein the alkyl alkanoate is methyl propanoate, the aldehyde is formaldehyde, and the product is methyl methacrylate.

13. The process of claim 1 comprising: (a) providing a gas feed stream comprising >1% of methane; (b) at least partially converting the methane via an OCM process to produce a gaseous first intermediate stream comprising water, other hydrocarbons, $H_2$, CO, $CO_2$, unreacted methane, and >1% of ethylene; (c) removing the majority of the water from the gaseous first intermediate stream to produce a gaseous second intermediate stream comprising ethylene, other hydrocarbons, $H_2$, CO, $CO_2$ and unreacted methane; and (d) contacting under carbonylation conditions the gaseous second intermediate stream, carbon monoxide gas, gaseous methanol and a solid sulfide-based metal catalyst to produce methyl propanoate.

14. The process of claim 1, wherein the solid, sulfide-based metal catalyst comprises cobalt.

\* \* \* \* \*